United States Patent
Domschke et al.

(10) Patent No.: US 6,897,271 B1
(45) Date of Patent: May 24, 2005

(54) POROUS HYDROGELS

(75) Inventors: Angelika Maria Domschke, Duluth, GA (US); Vimala Mary Francis, Suwanee, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/624,583

(22) Filed: Jul. 22, 2003

Related U.S. Application Data

(62) Division of application No. 09/755,443, filed on Jan. 5, 2001, now Pat. No. 6,653,420.
(60) Provisional application No. 60/174,460, filed on Jan. 5, 2000.

(51) Int. Cl.$^7$ .................................................. C08F 4/42
(52) U.S. Cl. ........................ 526/91; 526/258; 526/319; 526/320; 526/359; 526/317.1; 623/6.11
(58) Field of Search .......................... 526/91, 258, 319, 526/320, 317.1, 359; 623/6.11; 524/91, 359

(56) References Cited

U.S. PATENT DOCUMENTS

| | | | |
|---|---|---|---|
| 3,068,825 A * | 12/1962 | Knauf, Jr. et al. ............ 269/40 |
| 4,529,747 A | 7/1985 | Kato et al. | |
| 5,019,100 A | 5/1991 | Hennink et al. | |
| 5,583,191 A | 12/1996 | Kawai et al. | |
| 5,856,409 A * | 1/1999 | Ziemelis et al. ......... 525/330.2 |
| 5,922,249 A * | 7/1999 | Ajello et al. .................. 264/1.1 |
| 5,965,631 A * | 10/1999 | Nicolson et al. ............. 523/106 |
| 5,985,319 A * | 11/1999 | Embil et al. ................. 424/450 |
| 6,132,462 A | 10/2000 | Li | |
| 6,255,360 B1 * | 7/2001 | Domschke et al. ............ 521/64 |
| 6,653,420 B2 * | 11/2003 | Domschke et al. ......... 526/258 |
| 6,673,847 B2 * | 1/2004 | Jiang ............................ 521/56 |
| 2002/0077036 A1 * | 6/2002 | Roberts et al. ................ 451/41 |

FOREIGN PATENT DOCUMENTS

| | | |
|---|---|---|
| DE | 44 06 624 A1 | 9/1995 |
| FR | 71.45538 | 7/1972 |

* cited by examiner

*Primary Examiner*—Tatyana Zalukaeva
(74) *Attorney, Agent, or Firm*—Gardner Groff, P.C.

(57) ABSTRACT

The present invention relates to a process for the manufacture of a porous polymer; wherein a composition comprising a polymerizable component, a porogen having an inverse temperature dependent solubility and a solvent are polymerized at a temperature around the cloud point temperature of the composition. The porous polymers obtainable according to the process of the invention are useful, for example, as materials for the manufacture of biomedical devices and prostheses, including ophthalmic devices such as contact lenses or artificial corneas.

7 Claims, No Drawings

POROUS HYDROGELS

CROSS REFERENCE TO RELATED APPLICATIONS

This is a divisional of U.S. patent application Ser. No. 09/755,443, filed Jan. 5, 2001, now U.S. Pat. No. 6,653,420, which claimed priority to U.S. Provisional Patent Application Ser. No. 60/174,460, filed Jan. 5, 2000.

In many applications it has been found advantageous for polymers to be porous. The degree of porosity required depends on the application. For example, membrane filtration depends on the use of microporous polymers to effect separations of various materials. Macroporous sheets of chemically resistant polymers find extensive use as cell dividers in cells for electrolysis or electricity storage. Macroporous materials (open cell foams) produced through the use of blowing agents are used as cushioning materials. Porous materials have also found use in medicine as the medium for the dispensing of medicinal compounds, in medical implants for cell encapsulation or tissue ingrowth, and to achieve certain mechanical properties such as viscoelasticity.

Pores may be former in the polymer during the process of manufacturing an article of the desired shape or may be formed in the article after manufacture. A preferred process for the manufacture of porous polymers comprises the polymerization of a polymerizable component in the presence of an inert material often referred to as a porogen. Subsequent leaching of the porogen gives rise to interstices throughout the formed polymer material. However, this process is usually complicated by extensive extraction procedures necessary for a complete removal of the conventionally used porogens. A further possible disadvantage of this process is the difficulty of stabilising the suspension of porogen in the polymerization mixture. Unstable suspensions can lead to an non-homogeneous and unacceptable product. In many cases, extensive optimisation of the viscosity of the system and the type of porogen is needed to obtain a satisfactory result. In addition the procedure is limited in terms of the availability of porogens suitable for introducing the desired ranges of pore sizes. Beyond this, conventional porogens lead to a broad pore size distribution.

It now has surprisingly been found that specific surfactants, in particular surfactants with an inverse temperature dependent solubility, contribute to a narrow pore size distribution and greatly simplify porogen-removal after the polymerization process. Used as porogens, these surfactants offer an advantage in the preparation of porous matrices due to their unique inverse temperature dependent solubility property. With the proper choice of a porogen having a specific cloud point temperature, it is possible to achieve a system or formulation where the porogen forms a homogeneous phase with the polymerizable components before the cure. Due to their inverse temperature dependent solubility behavior, the porogens form aggregates during the cure at a temperature around the cloud point temperature of the composition. Therefore, curing of this formulation around its cloud point temperature leaves an imprint of the defined aggregation structure of the surfactants in the polymerized hydrogel membranes. These aggregates are then easily removed from the matrix polymer at a temperature below their cloud point in a suitable extraction medium that swells the polymer, leaving a porous hydrogel behind with a narrow pore size distribution created by the aggregated porogen that is now removed. In addition, different porogens impart different levels of porosity to the hydrogel membranes.

Hence, an object of the present invention is to provide a process for the manufacture of a hydratable porous polymer comprising the steps of:
(a) providing a homogeneous composition at a temperature below the cloud point temperature of the composition comprising
  (i) a polymerizable component that comprises at least one polymerizable hydrophilic monomer or macromer,
  (ii) a porogen having an inverse temperature dependent solubility, and
  (iii) a solvent;
(b) subjecting the composition to a polymerization reaction at or above the cloud point temperature of the composition; and
(c) removing the porogen from the resulting porous polymer at a temperature below the cloud point temperature of the composition.

The polymerizable component according to step (a) may in principle contain any hydrophilic ethylenically unsaturated compound as long as the composition as a whole is homogenious at easy accessible temperatures, for example at room temperature, and the inverse temperature dependent solubility of the porogen is retained in the formulation. Examples of polymerizable hydrophilic monomers that may be part of the polymerizable component according to step (a) are, for example, (i) acrylic or methacrylic acid; (ii) a $C_1$–$C_-$-alkyl ester of acrylic or methacrylic acid which may be substituted in the alkyl portion by hydroxy; (iii) acrylamide or a N-mono- or N,N-di-$C_1$–$C_4$-alkyl acrylamide, for example N,N-dimethyl acrylamide; (iv) a 5- or 6-membered heteroaromatic or heteroaliphatic monomer having one N-atom and in addition no further heteroatom or an additional N— or O— heteroatom, or a 5 to 7-membered lactame, for example N-vinylpyrrolidon, N-vinylimidazol, N-vinyl-2-methylimidazol or N-acryloyl morpholine; (v) a sulfocontaining monomer, preferably an ethylenically unsaturated compound having from 2 to 18 C-atoms which is substituted by a sulfo group or a suitable salt thereof, for example methallyl-sulfonic acid, styrenesulfonic acid, sulfopropylmethacrylate, sulfopropylacrylate, 2-acrylamido-2-methylpropanesulfonic acid, vinyl sulfonic acid, or a suitable salt thereof, for example an alkaline salt or ammonium salt, in particular the sodium or potassium salt; or (vi) allyl alcohol, vinyl acetate or vinyl alcohol, which can be used in each case alone, or in mixtures with other ethylenically unsaturated monomers.

A suitable hydrophilic macromer that the polymerizable component may comprise is, for example, a vinylfunctionalized polyvinyl alcohol, polyalkylene oxide or N-vinylpyrrolidone homo- or copolymer. The macromer may contain one or more than one ethylenically unsaturated double bond. A preferred hydrophilic macromer is a vinyl-functionalized polyvinyl alcohol or polyethylene oxide, in particular a vinylfunctionalized polyvinyl alcohol, for example as described in U.S. Pat. No. 5,508,317, issued to Beat Müller on Apr. 16, 1996, which is incorporated herein by reference. The weight average molecular weight of the hydrophilic macromer may vary within wide limits; a suitable range is from about 2000 up to 1,000,000. Preferably, the hydrophilic macromer has a molecular weight of up to 300,000, especially up to approximately 100,000 and especially preferably from about 5000 to about 50,000.

In a preferred embodiment of the invention the polymerizable component comprises one or more different hydrophilic monomers selected from the group consisting of hydroxyethyl acrylate, hydroxyethyl methacrylate, N-vinyl pyrrolidone, acrylic acid, methacrylic acid, acrylamide, N,N-dimethyl acrylamide, N-acryloyl morpholine, vinyl acetate, vinyl alcohol, methallylsulfonic acid, styrenesulfonic acid, sulfopropylmethacrylate, sulfopropylacrylate, 2-acrylamido-2-methylpropanesulfonic acid, vinyl sulfonic acid, and a suitable salt thereof.

An even more preferred embodiment of the invention concerns a polymerizable component comprising one or more different monomers selected from the group consisting of hydroxyethyl methacrylate, N-vinyl pyrrolidone, acrylamide, N,N-dimethyl acrylamide, sodium methallylsulfonate, sodium styrenesulfonate, potassium sulfopropylmethacrylate and potassium sulfopropylacrylate.

In addition, the polymerizable component may contain a low molecular weight crosslinker. A suitable crosslinker, if present, is, for example, a low molecular weight di- or polyvinylic crosslinking agent such as ethylenglycol diacrylate or dimethacrylate, di-, tri- or tetraethylen-glycol diacrylate or dimethacrylate, allyl (meth)acrylate, a $C_2$–$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or -bismethacrylamide, ethylene bisacrylamide or ethylene bismethacrylamide, triallyl phthalate or diallyl phthalate. The average weight average molecular weight of the crosslinker is, for example, up to 1000, preferably up to 750 and most preferably up to 500. Preferred crosslinkers according to the invention are ethyleneglycol-dimethacrylate, pentaerythritoltetraacrylate or pentaerythritoltetramethacrylate. The polymerizable component according to step (a) preferably comprises a low molecular weight crosslinker.

Preferably, the polymerizable component consists of 50 to 99.9% by weight of one or more different ethylenically unsaturated monomers and from 0.1 to 50% by weight of a low molecular weight crosslinker. More preferably, the polymerizable component consists of 80 to 99.5% by weight of one or more different ethylenically unsaturated monomers and from 0.5 to 20% by weight of a low molecular weight crosslinker. Even more preferably, the polymerizable component consists of 85 to 99.5% by weight of one or more different ethylenically unsaturated monomers and from 0.5 to 15% by weight of a low molecular weight crosslinker.

A preferred polymerizable component consists of one or more monomers selected from the group consisting of hydroxyethyl methacrylate, N-vinyl pyrrolidone, acrylamide, N,N-dimethyl acrylamide, sodium methallylsulfonate, sodium styrenesulfonate, potassium sulfopropylmethacrylate and potassium sulfopropylacrylate and of a low molecular weight crosslinker selected from the group consisting of ethyleneglycol-dimethacrylate, pentaerythritoltetraacrylate or pentaerythritoltetramethacrylate. A particularly preferred polymerizable component consists of hydroxyethyl methacrylate or of a mixture of hydroxyethyl methacrylate and a sulfomonomer selected from the group consisting of sodium methallylsulfonate, sodium styrenesulfonate, potassium sulfopropylmethacrylate and potassium sulfopropylacrylate, and of a low molecular weight crosslinker selected from the group consisting of ethyleneglycol-dimethacrylate, pentaerythritoltetraacrylate or pentaerythritoltetramethacrylate.

The amount of polymerizable component (i) that is present in the composition according to step (a) may vary within wide limits. A suitable weight range of the polymerizable component is, for example, from 10 to 94% by weight, preferably from 20 to 90% by weight and most preferably from 25 to 85% by weight, in each case relative to the entire weight of the composition of step (a).

The porogen may in principle be any compound that forms a homogenious solution with the polymerizable component at convenient temperatures, in particular at room temperature, and which retains its inverse temperature dependent solubility property in the composition. A screening method for investigating inverse temperature dependent solubility (ITDS) characteristics of a formulation is given below in the working examples. A group of suitable porogens are, for example, polyalkylene block copolymers, such as polyethylene-polypropylene, polyethylene-polybutylene or polyethylene-polypropylene-polybutylene block copolymers, in particular polymeric surfactants belonging to the class of block copolymers of poly(ethylene oxide) (PEO) and poly(propylene oxide) (PPO) of the formula PEO-PPO-PEO, called Normal Pluronics, or of the formula PPO-PEO-PPO, called Reverse Pluronics, which are commercially available under the trade names Pluronics® and Tetronics®, having a range of chemical structures, molecular weights and sizes. These Pluronics have a unique property called the "inverse temperature dependent solubility" which implies that in specific solvents the polymer solubility decreases with increasing temperature. The temperature at which the polymer phase separates is called the "cloud point" or the "critical solution temperature". Dependent on their chemical structure and molecular weight, Pluronics have different cloud points which may vary within wide limits, for example between room temperature or lower and 100° C. or preferably between 30° C. and 100° C.

The amount of porogen (ii) that is present in the composition according to step (a) may vary within wide limits. A suitable weight range of the porogen is, for example, $\geq 3\%$ by weight, advantageously from 3 to 85% by weight, preferably from 3 to 50% by weight, more preferably from 5 to 40% by weight, and most preferably from 5 to 25% by weight, in each case relative to the entire weight of the composition of step (a).

Suitable solvents according to step (a) include, for example, water, $C_1$–$C_4$-alkanols, $C_1$–$C_6$-alkylamines, $C_2$–$C_6$-alkylethers, $C_1$–$C_4$-alkyl esters of carboxylic acids such as ethyl acetate, carboxy amides such as N,N-dimethyl formamide, fluorinated alkanols, and mixtures thereof. In most cases such solvents are added to reduce viscosity of the solution or to make the solution easier to dispense, for example into molds. A preferred solvent is water, a $C_1$–$C_2$-alkanol or a mixture thereof. In case of a Pluronics® as porogen the solvent is water or an aqueous solution comprising for example one of the above-mentioned organic solvents, and is in particular water. The amount of solvent that is present in the composition according to step (a) may vary within wide limits. A suitable weight range of the solvent (iii) is, for example, from 3 to 75% by weight, preferably from 5 to 60% by weight and most preferably from 5 to 55% by weight, in each case relative to the entire weight of the composition of step (a).

The composition according to step (a) may contain further components, for example a polymerization initiator. Suitable polymerization initiators are typically those that are initiating a radical polymerization of ethylenically unsaturated compounds. The radical polymerization may be induced thermally, or preferably by UV irradiation. Redox initiation may also be used.

Suitable thermal polymerization initiators are known to the skilled artisan and comprise for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis (isobutyronitrile), 1,1'-azo-bis (1-cyclohexanecarbonitrile), 2,2'-azo-bis(2,4-dimethylvaleronitrile), 4,4'-azo-bis(4-cyanovaleric acid and the like.

Initiators for the radiation-induced polymerization, so-called photoinitiators, may belong to different types, for example to the thioxanthone type ord to the benzoin type. Useful photoinitiators include for example benzophenones substituted with an ionic moiety, a hydrophilic moiety or both such as 4-trimethylaminomethyl benzophenone hydrochloride or benzophenone sodium 4-methanesulfonate; benzoin $C_1$–$C_4$alkyl ether such as benzoin methyl ether; thioxanthones substituted with an ionic moiety, a hydrophilic moiety or both such as 3-(2-hydroxy-3-trimethylaminopropoxy) thioxanthone hydrochloide, 3-(3-trimethylaminopropoxy) thioxanthone hydrochloride, thioxanthone 3-(2-ethoxysulfonic acid) sodium salt or thioxanthone 3-(3-propoxysulfonic acid) sodium salt; or phenyl ketones such as 1-hydroxycyclohexylphenyl ketone, (2-hydroxy-2-propyl)(4-diethylene glycol phenyl) ketone, (2-hydroxy-2-propyl)(phenyl-4-butanecarboxylate)ketone; or commercial products such as Darocure™ or Irgacure™ types, e.g. Darocure 1173 or Irgacure 2959.

The composition according to step (a) preferably comprises a polymerization initiator, in particular a photoinitiator. The polymerization initiator is present in an amount of, for example, 0.05 to about 1.5% by weight, preferably 0.1 to 1.0% by weight and particularly preferably 0.08 to 0.5% by weight, based on the entire polymerizable component in each case.

Minor amounts of property modifying components may optionally be added to the mixture before polymerization.

The polymerizable component may be mixed with the porogen, the solvent and other optional components by any convenient means. For example the polymerizable component may be mixed with the porogen, the solvent and other optional components by shaking or stirring. The order in which the components are added to the mixture is not narrowly critical. The mixing of the components is performed at a temperature below the cloud point temperature of the resulting composition, for example at a temperature of from about 0 to 80° C., preferably from 5 to 50° C., more preferably from 10 to 30° C. and in particular at room temperature.

The compositions of the invention may be polymerized by any convenient method generally as described above with reference to the initiation of the polymerizable component. Suitable polymerization conditions will be apparent to those skilled in the art. The compositions are cured at a temperature at or above the cloud point temperature of the mixture. The cloud point temperature of a preferred composition according to the invention using, for example, a Pluronics® porogen is typically in the range of from about 30 to 60° C., preferably from about 30 to 45° C. and most preferably of from about 30 to 40° C. Accordingly, the polymerization reaction is advantageously carried out at a temperature within the above given temperature ranges. According to a preferred embodiment of the process of the invention, the temperature inside the curing chamber is kept constant at the desired curing temperature, that is at a temperature at or above the cloud point temperature of the composition to be cured, and the homogenious composition of the polymerizable component, the porogen, the solvent(s) and other optional components is inserted into the curing chamber just before the commencement of the curing. The polymerization time may vary within wide limits but is suitably chosen as to be in the range of from about 1 minute to 1 hour, preferably from about 3 to 30 minutes and most preferably from 5 to 15 minutes.

After the polymerization reaction the porogen, solvent(s) and the like may be removed from the porous polymer by any convenient means. Suitable means for removal of the porogen (or solvent) include solvent extraction, washing or leaching. Preferred means for removal of the porogen are solvent extraction and washing. Typically, the removal of the porogen is carried out a temperature below the cloud point temperature of the porogen. Preferably, the resulting porous polymers are first of all extracted at room temperature in a suitable swelling solvent, such as in a $C_1$–$C_4$-alcohol or in a mixture of water and a $C_1$–$C_4$-alcohol, followed by a treatment with water. Following extraction, the resulting porous polymers are preferably equilibrated in water.

The process of the present invention is useful for generating materials of various pore sizes and morphologies. The upper limit of average pore size of individual pores is about 5 microns, with 100 nanometres being typical, while pores of around 10 nanometres in diameter may also be obtained.

The polymers prepared according to the present invention have a water content which is, when fully swollen in water, between about 30 and about 70 weight percent. In addition, the polymers that are obtainable according to the process of the invention exhibit a narrow pore size distribution. In case of a small size porogen this leads to polymers with a high optical clarity, which makes them useful for biomedical applications, particularly for ophthalmic devices such contact lenses. In case of larger size porogens translucent or turbid polymers are obtained which are, for example, useful as membranes. Since the size of the pores can be selected by using a specific porogen it is possible to make the polymers selectively permeable to small proteins like vitamin B-12 or albumin.

In one embodiment the porous polymer may be in the form of a closed-cell structure with discrete pores dispersed throughout the polymer.

In a further preferred embodiment the pores may form an interpenetrating network. It is more useful to characterise these morphologies in terms of permeability of the polymer to molecules of defined molecular weight.

The form of the polymeric material may vary within wide limits. Examples are particles, granules, capsules, fibres, tubes, films or membranes, preferably moldings of all kinds such as ophthalmic moldings, in particular contact lenses.

The polymers of the invention are characterized in particular by a high biocompatibility, biostability, noncytotoxicity, cell growth capability and antifouling properties. Said properties make them suitable as materials for the attachment and growth of human or animal cells in vivo or in vitro, medical implants (such as implantable semipermeable membrane materials, tissue implants in cosmetic surgery, implants containing hormone secreting cells such as pancreatic islet cells, breast implants, artificial joints and the like), in artificial orgrans, tissue culture apparatus (such as bottles, trays, dishes and the like), in biological reactors (such as those used in the production of valuable proteins and other components by cell culture), in optical instruments, such as microscope slides and the like. The polymers obtainable according to this invention are especially suitable for materials that are designed for long-term implantation.

Ocular prostheses, such as corneal implants, may be made by polymerization in moulds as described above and, optionally, the resultant polymer may be fabricated or machined to the desired conformation.

Corneal implants may be placed by way of conventional surgical techniques beneath, within, or through corneal epithelial tissue, or within the corneal stroma or other tissue layers of the cornea. Such implants may change the optical properties of the cornea (such as to correct visual deficiencies) and/or change the appearance of the eye, such as pupil colouration. A corneal implant may comprise an optical axis region which on implantation covers the pupil and provides visual acuity and a less transparent region which surrounds the periphery of the optical axis region. Alternatively the implant may have the same visual acuity across its dimensions.

The polymers produced according to the present invention may be formed into other useful articles using conventional moulding and processing techniques as are well known in the art. Given the visual transparency of the polymers of the present invention, they may find use in tissue culture apparatus, optical instruments, microscope slides and the like.

A further aspect of this invention is the use of the porous hydrogel in film or sheet form as a membrane or a filter. Such porous film may be laminated with another support film to form a composite. Such applications may involve permeability to gases or liquids.

The porous polymers of the present invention may be suitable, for example, for use in the fields of membrane filters and separation, in the field of industrial biotechnology, and in the biomedical field.

Examples for the field of membrane filters and separation are industrial membranes, e.g. for micro filtration and ultra filtration, for example in the food, dairy, juice, or low alcohol beer industries, waste water treatment, home reverse osmosis, or membrane distillation using osmotic pressure.

Examples or the field of industrial biotechnology are supports for synthetic and biological ligands or receptors for bioreactors and biosensors, sustained release devices for active compounds, or capacitors.

Further examples for the biomedical field, besides ophthalmic devices, are dialysis and blood filtration, encapsulated biological implants, e.g. pancreatic islets, implanted glucose monitors, drug delivery patches and devices, wound healing and dressing, artificial skin, vascular grafts, regenerative templates or patches for wound healing, (soft) tissue augmentation, percutaneous fixation devices or artificial organs. The present invention is further described in the following non-limiting examples. If not other wise specified, all parts are by weight. Temperatures are in degrees Celsius. Molecular weights of macromers or polymers are weight average molecular weights if not otherwise specified.

Preparation of Formulation

EXAMPLES 1–3

A formulation is prepared in each case using the following procedure. The exact weights and weight percentages of the components used in the formulation are listed in Table 1 below. The components, hydroxyethyl methacrylate (HEMA), crosslinker (ethylene glycol dimethacrylate or EGDMA), porogen (Pluronic® L62, L44, or P103) and water are added to a clean, dry, labeled 20 ml scintillation vial. Water is added to the above mixture and the contents are allowed to mix until a homogeneous mixture is obtained. The initiator (Darocur 1173) is added to the above mixture. The vial is placed on a vortex for about a minute to enable efficient mixing of formulation components. The final formulation is clear and completely homogeneous at room temperature.

Inverse Temperature Dependent Solubility Characteristics

Various formulations are screened for inverse temperature-dependent solubility characteristics. The typical procedure followed to check this property is given below.

The respective formulation is taken in a vial with all of the above components (HEMA, EGDMA, water and porogen) except the initiator. The vial is swirled in a water bath at a specific temperature (temperature monitored by a thermometer) to determine the cloud point of the formulation. The temperature at which the formulation turns cloudy (detected visually) is determined to be the cloud point of the formulation. The vial containing the cloudy formulation is swirled in a water bath containing ice water, at which point the formulation turns clear. This visual test is done to determine if the formulation exhibits an inverse temperature-dependent solubility property in the temperature range of interest. The temperature range of interest is determined to be at or around the curing temperature. The formulations that exhibit the inverse temperature-dependent solubility property in this manner are screened for consideration. However, formulations tested in this manner are not used for curing. Repeat experiments are performed to prepare formulations for casting purposes.

Degassing, Casting, and Curing

The vial containing one of the formulations is sealed with a rubber septum and the contents are degassed for 5 minutes under a slow to medium flow of nitrogen. The formulation is stirred during the degassing procedure. The nitrogen flow is maintained throughout the degassing and casting process at a steady rate.

While the contents are being degassed, the respective molds (flat molds of 200 um thickness) are arranged in suitable frames for subsequent casting. Once the degassing is complete, the formulation is carefully removed with a syringe. The required amount is quickly transferred into the lower mold (female portion), and closed immediately with the upper mold (male portion) to enable a tight seal. This procedure is repeated for all molds. The metal frames are attached and tightened with clamps. A UV box is used for the polymerization which is left for 60 minutes before cure in order to adjust a constant temperature of 33 to 36° C. inside the box. The molds are placed into the box and polymerized at this temperature for 30 minutes (UV intensity of 3 mW/cm$^2$).

Extraction of Cured Lenses

The frames are removed from the UV box and allowed to cool for a few minutes. The removal of lenses from the molds (or the demolding process) is done manually. The demolded lenses are placed inside perforated plastic cages. The cages containing the lenses are immersed in a beaker containing the suitable extracting solvent. Typically, the extraction is done in 50%. IPA: 50% H$_2$O overnight, followed by extraction in 25% IPA: 75% water for 4 h (with 4 exchanges), followed by extraction in ice for 4 h (with 4 exchanges), followed by extraction in water for 1 h. Once the extraction and equilibration into water is complete, the lenses are removed from cages and transferred to clean bottles containing water. These are analyzed for water content.

Analysis Performed

Water content measurements are performed on the prepared lenses. The water contents are measured using the following procedure. The wet lenses are tap dried on a lint free paper and transferred to a previously weighed clean vial. After the required number of lenses (typically 7 to 10) is placed in the vial, the weight of the wet lenses is recorded. The vial is immediately covered with a piece of aluminum foil, and tiny holes are pierced through the foil to enable efficient drying. The vial is placed inside a vacuum oven and dried overnight at a temperature of 100° C. at a pressure of 30 mm Hg. The weight of the vial with the dry lenses is determined at room temperature.

The water content in percent is determined from the following ratio,

[(Weight of wet lenses−Weight of dry lenses)÷(Weight of hydrated or wet lenses)]×100

TABLE 1

| Example No. | 1 | 2 | 3 |
|---|---|---|---|
| HEMA [g]/[% by weight] | 4.0/33.3 | 2.0/30.2 | 4.0/33.6 |
| Pluronic L 62 [g]/[% by weight] | 1.8/15.2 | — | — |
| Pluronic L 44 [g]/[% by weight] | — | 1.5/22.8 | — |
| Pluronic P 103 [g]/[% by weight] | — | — | 1.8/15.1 |
| EGDMA [g]/[% by weight] | 0.1/0.8 | 0.1/1.5 | 0.1/0.8 |
| Darocure [g]/[% by weight] | 0.02/0.2 | 0.01/0.2 | 0.02/0.2 |
| Water [g]/[% by weight] | 6.1/50.5 | 3.0/45.3 | 6.0/50.3 |
| Total [g]/[% by weight] | 12.0/100 | 6.6/100 | 11.9/100 |
| Water contents after curing [%] | 44 | 38 | 58 |

EXAMPLES 4–10

The components as given in Table 2 below are mixed and degassed by a stream of argon through the mixture for 30 minutes. 100 µl of the mixture is then dispensed via a syringe into one polypropylene mold and the mold is then closed in each case. A UV box is used for the polymerization which is left for 60 minutes before cure in order to adjust a constant temperature of 33 to 36° C. inside the box. The molds are placed into the box and polymerized at this temperature for 10 minutes (UV intensity of 6 mW/cm$^2$). After opening the polymerized samples are extracted as described in Example 1 above, and are then equilibrated into water and autoclaved. CGI and Cell outgrowth tests reveal no cytotoxicity and attachment and growth of fibroblast cells.

TABLE 2

(amounts are given as parts by weight)

| Example No. | 4 | 5 | 6 | 7 | 8 | 9 | 10 |
|---|---|---|---|---|---|---|---|
| HEMA | 95 | 90 | 85 | 85 | 95 | 95 | 95 |
| Sulfo 1 | 5 | 10 | 15 | — | 5 | 5 | 5 |
| Sulfo 2 | — | — | — | 15 | — | — | — |
| Pluronic L62 | 10 | 10 | 10 | 10 | 30 | — | — |
| Pluronic F68LF | — | — | — | — | — | 20 | 30 |
| Crosslinker 1 | 10 | 10 | 10 | 10 | — | 1 | 1 |
| Crosslinker 2 | — | — | — | — | 2 | — | — |
| PVP | — | — | — | — | 2.75 | 3 | 3 |
| Darocure | 0.3 | 0.3 | 0.3 | 0.3 | 0.3 | 0.3 | 0.3 |
| Water | 11 | 11 | 11 | 11 | 50 | 11 | 11 |

HEMA = 2-hydroxyethylmethacrylate; PVP = polyvinylpyrrolidone; Pluronic L62, F68LF = triblock copolymers of {[polyethylene oxide] – [polypropylene oxide] – [polyethylene oxide]}; Sulfo 1 = 3-sulfopropyl methacrylate; Sulfo 2 = 3-sulfoprupul acrylate; Crosslinker 1 = pentaerythritol tetraacrylate; Crosslinker 2 = ethyleneglycol dimethacrylate; Darocure = Darocure 1173.

Table 3 shows the properties of the hydrogels generated from the formulations of Table 2, proving the excellent cell growth capability and high water content.

TABLE 3

| No. | Optical property | Cell Growth* | water content % |
|---|---|---|---|
| 4 | transparent | 2 | 40 |
| 5 | transparent | 3 | 43 |
| 6 | transparent | 2 | 54 |
| 7 | transparent | 2 | 49 |
| 8 | transparent | 1 | 78 |
| 9 | transparent | 3 | 61 |
| 10 | transparent | 2 | 64 |

*3 = very good; 2 = good; 1 = less good

What is claimed is:

1. A hydratable porous polymer molding comprising a composition of at least one polymerizable hydrophilic monomer or macromer, an inert porogen having an inverse temperature-dependent solubility which can be retained in the composition, and a solvent;

wherein the molding is formed by providing said composition at a temperature below the cloud point temperature of the composition, subjecting the composition to a polymerization reaction at a temperature around the cloud point temperature of the composition, and removing the porogen from the resulting porous polymer at a temperature below the cloud point temperature of the composition.

2. A molding according to claim 1, which is a biomedical device.

3. A molding according to claim 2, which is a medical implant.

4. A molding according to claim 2, which is an ocular prosthesis.

5. A molding according to claim 2, which is an implantable intraocular lens or artificial cornea.

6. A hydratable porous polymer material comprising a composition of at least one polymerizable hydrophilic monomer or macromer, an inert porogen having an inverse temperature-dependent solubility which can be retained in the composition, and a solvent;

wherein the composition is polymerized at a temperature around the cloud point temperature of the composition, and the porogen is removed from the resulting porous polymer at a temperature below the cloud point temperature of the composition.

7. The hydratable porous polymer material of claim 6, wherein the composition is polymerized in a mold.

* * * * *